United States Patent [19]

Jakobson et al.

[11] Patent Number: 5,247,114
[45] Date of Patent: Sep. 21, 1993

[54] POLYGLYCERINE AND CAPRIC ACID ESTER MIXTURE

[75] Inventors: Gerald Jakobson; Werner Siemanowski, both of Rheinberg; Karlheinz Uhlig, Krefeld-Traar zu nennen, all of Fed. Rep. of Germany

[73] Assignee: Deutsche Solvay-Werke, Solingen, Fed. Rep. of Germany

[21] Appl. No.: 838,330

[22] Filed: Feb. 20, 1992

[30] Foreign Application Priority Data

Feb. 20, 1991 [DE] Fed. Rep. of Germany ....... 4105305

[51] Int. Cl.$^5$ .................... C07C 59/235; C11C 3/02
[52] U.S. Cl. ...................................... 554/227; 554/168
[58] Field of Search ............... 554/227, 168; 514/547, 514/552

[56] References Cited

FOREIGN PATENT DOCUMENTS

| 0299295A2 | 7/1988 | European Pat. Off. |
| 3041073 | 10/1980 | Fed. Rep. of Germany |
| 3902374 | 1/1989 | Fed. Rep. of Germany |
| 451461 | 2/1991 | Fed. Rep. of Germany |

OTHER PUBLICATIONS

Chemical Abstracts, vol. 110, #22, p. 127, 1989 195184h.

*Primary Examiner*—José G Dees
*Assistant Examiner*—Deborah D. Carr
*Attorney, Agent, or Firm*—Foley & Lardner

[57] ABSTRACT

The present invention relates to a fatty acid polyglycerol ester mixture containing a $C_8$ to $C_{24}$ fatty acid ester component comprising (A) about 20 to 80% by weight of fatty acid monoester of a polyglycerol containing more than about 40% of $C_{10}$ and/or $C_8$ in the ester component of the polyglycerol; (B) about 80 to 20% by weight of fatty acid diester of polyglycerol; and (C) about 15 to 0% by weight of tri- and higher esters of the polyglycerol containing than about 40% of $C_{10}$ and/or $C_8$ in the ester component of the polyglycerol; and further wherein the resulting fatty acid polyglycerol ester mixture comprises (A) about 20 to 45% by weight of fatty acid diglycerol ester; (B) about 30 to 45% by weight of fatty acid triglycerol ester; and (C) about 50 to 10% by weight of fatty acid tetra- and higher polyglycerol esters. A thickened composition, skincare composition and a cleansing agent containing the fatty acid polyglycerol ester mixture as a component thereof and a process for the preparation of the fatty acid polyglycerol ester mixture are disclosed.

29 Claims, No Drawings

POLYGLYCERINE AND CAPRIC ACID ESTER MIXTURE

FIELD OF THE INVENTION

The present invention relates to a fatty acid polyglycerol ester mixture characterized by a very specific composition, distribution of the fatty acid esters and chain lengths in the ester group, to products containing the fatty acid polyglycerol ester mixture as a component thereof including a thickened composition, skincare composition, and a cleansing agent and to a process for the preparation of the fatty acid polyglycerol ester mixture.

BACKGROUND OF THE INVENTION

A cleansing agent which contains $C_8$ to $C_{18}$ monofatty acid esters of diglycerol and/or $C_8$ to $C_{18}$ difatty acid esters of tetraglycerol in addition to an ionogenic and/or amphoteric surfactant is disclosed in DE-A 39 02 374. This cleansing agent has the following advantageous characteristics: (i) suitability in further processing applications, (ii) compatibility with skin, and (iii) biological degradability.

This agent, however, has the following disadvantageous characteristics: (i) preparation requires a multistage process which is relatively expensive and labor intensive, and (ii) it is normally produced as a solid product. During further processing of the agent, i.e., into preparations, processing difficulties occur. Exemplary of these processing difficulties is the clogging of supply and metering devices because the agent cannot be pumped at room temperature. In order to dissolve the agent, heat and/or strong shearing forces must be applied.

In DE-C 30 41 073, wool wax substitutes are disclosed which are based on ester mixtures composed of 1 mol of a glycerol/polyglycerol mixture, esterified with 0.5 to 1.1 mol of one or more saturated aliphatic monocarboxylic acids having 6 to 10 C atoms, 0.5 to 1.1 mol of one or more saturated aliphatic monocarboxylic acids having 16 to 22 C atoms, 0.0 to 0.6 mol of one or more aliphatic saturated branched-chain monocarboxylic acids having 16 to 18 C atoms, 0.0 to 0.5 mol of one or more saturated hydroxymonocarboxylic acids having 16 to 20 C atoms and 0.5 to 1.0 mol of one or more saturated aliphatic dicarboxylic acids having 4 to 10 C atoms. These mixtures are prepared, inter alia, using dicarboxylic acids in such a manner that crosslinked water-insoluble compounds are formed which possess other chemical and physical properties.

Accordingly, a need exists for a fatty acid polyglycerol ester mixture which can be prepared economically in a simple process and is liquid at ambient temperature in order to facilitate its suitability for use in further processing operations. Further, it would be advantageous if such a mixture was suitable for use in thickening, refatting and skin care applications and was non-toxic and ecologically safe.

SUMMARY OF THE INVENTION

It is therefore an object of the present invention to provide a fatty acid polyglycerol ester mixture which: can be prepared economically in a simple process; is liquid at ambient temperature in order to facilitate its use in further processing operations; exhibits properties that are useful for thickening, refatting and skin care applications; and is non-toxic and ecologically safe.

It is a further object of the present invention to provide a thickened composition containing as a thickening agent a fatty acid polyglycerol ester mixture containing a $C_8$ to $C_{24}$ fatty acid component.

It is yet a further object of the present invention to provide a skincare composition containing as an additive a fatty acid polyglycerol ester mixture containing a $C_8$ to $C_{24}$ fatty acid component.

It is still another object of the present invention to provide a cleansing agent containing as a surfactant a fatty acid polyglycerol ester mixture containing a $C_8$ to $C_{24}$ fatty acid component.

In accomplishing the foregoing objects, there has been provided, in accordance with one aspect of the present invention, a fatty acid polyglycerol ester mixture comprising a $C_8$ to $C_{24}$ fatty acid ester component, wherein the fatty acid polyglycerol ester mixture, relative to 100 parts by weight of the fatty acid polyglycerol ester mixture, is comprised of (A) about 20 to 80% by weight fatty acid monoester of a polyglycerol containing more than about 40% of $C_{10}$ and/or $C_8$ in the saturated fatty acid ester component of a polyglycerol; (B) about 80 to 20% by weight fatty acid diester of a polyglycerol; and (C) about 15 to 0% by weight tri- and higher esters of a polyglycerol containing more than about 40% of $C_m$ and/or $C$: in the saturated fatty acid ester component of the poly-glycerol; and further wherein the resulting fatty acid polyglycerol ester mixture comprises (A) about 20 to 45% by weight of fatty acid diglycerol ester; (B) about 30 to 45% by weight of fatty acid triglycerol ester; (C) about 50 to 10% by weight of fatty acid tetra- and higher polyglycerol esters; and (D) about 5 to 0% by weight free polyglycerol.

In a preferred embodiment, a fatty acid polyglycerol ester mixture, relative to 100 parts by weight of the fatty acid polyglycerol ester mixture, comprises (A) about 35 to 65% by weight of fatty acid monoester of a polyglycerol containing about 50% or more of $C_{10}$ and/or $C_8$ in the saturated fatty acid ester component of the polyglycerol; (B) about 65 to 35% by weight fatty acid diester of a polyglycerol; and (C) about 7 to 0.5% by weight tri- and higher esters of a polyglycerol containing about 50% or more of $C_m$ and/or $C$: in the saturated fatty acid ester component of the polyglycerol; and further wherein the resulting fatty acid polyglycerol ester mixture comprises (A) about 25 to 42% by weight fatty acid diglycerol ester; (B) about 32 to 43% by weight fatty acid triglycerol ester; (C) about 43 to 15% by weight fatty acid tetra- and higher polyglycerol esters and (D) about 2.5 to 0% by weight free polyglycerol.

In accordance with yet another aspect of the present invention, a fatty acid polyglycerol ester mixture is provided comprising about 20 to 80% by weight fatty acid monoester of a polyglycerol ester component of the polyglycerol.

In a preferred embodiment, a fatty acid polyglycerol ester mixture is provided comprising (A) about 35 to 65% by weight fatty acid monoester of a polyglycerol containing more than about 50%, $C_{10}$ and/or $C$: in the ester component of the polyglycerol.

In another preferred embodiment, about 0 to 45%, or more preferably about 0 to 30%, fatty acid monoesters containing $C_{12}$ to $C_{18}$ comprise the saturated fatty acid ester component and/or fatty acid monoesters containing $C_{12}$ to $C_{24}$ comprise the unsaturated fatty acid component. Other preferred embodiments are comprised of (A) about 80 to 20% by weight, or more preferably about 65 to 35% by weight, fatty acid diesters of a polyglycerol and (B) about 15 to 0% by weight, or more preferably about 7 to 0.5% by weight, tri- and higher esters of a polyglycerol containing more than 40%, or more preferably more than about 50%, $C_{10}$ and/or $C_8$ in the ester component of the polyglycerol. Other preferred embodiments are comprised of (A) about 0 to 45%, or more preferably about 0 to 30%, fatty acid diesters each containing $C_{12}$ to $C_{18}$ in the saturated fatty acid component and/or fatty acid diesters containing $C_{12}$ to $C_{24}$ in the unsaturated fatty acid ester component, and further wherein the resulting fatty acid polyglycerol ester mixture comprises (A) about 20 to 45% by weight fatty acid diglycerol ester; (B) about 30 to 45% by weight fatty acid triglycerol ester; (C) about 50 to 10% by weight fatty acid tetra- and higher polyglycerol esters; and (D) about 5 to 0%, or more preferably about 2.5 to 0%, free polyglycerol.

In another preferred embodiment, the ester group of a polyglycerol within the present invention is comprised of more than about 90% by weight, or more preferably more than about 94% by weight, $C_{10}$ and/or $C_8$.

In accordance with a further aspect of the present invention, a thickened composition is provided containing as a thickening agent a fatty acid polyglycerol ester mixture within the present invention comprising, relative to 100 parts by weight of the fatty acid polyglycerol ester mixture, (A) about 20 to 80% by weight of fatty acid monoester of a polyglycerol containing more than about 40% of $C_{10}$ and/or $C_8$ in the ester component of the polyglycerol; (B) about 80 to 20% by weight of fatty acid diester of a polyglycerol; and (C) about 15 to 0% by weight of tri- and higher esters of a polyglycerol containing more than about 40% of $C_{10}$ and/or $C_8$ in the ester component of the polyglycerol; and further wherein the resulting fatty acid polyglycerol ester mixture comprises (A) about 20 to 45% by weight of fatty acid diglycerol ester; (B) about 30 to 45% by weight of fatty acid triglycerol ester; (C) about 50 to 10% by weight of fatty acid tetra- and higher polyglycerol esters; and (D) about 5 to 0% by weight free polyglycerol.

In accordance with still another aspect of the present invention, a thickened composition is provided containing as a thickening agent a fatty acid polyglycerol ester mixture within the present invention comprising, relative to 100 parts by weight of the fatty acid polyglycerol ester mixture, (A) about 35 to 65% by weight of fatty acid monoester of a polyglycerol containing at least about 50% of $C_{10}$ and/or $C_8$ in the ester component of the polyglycerol; (B) about 65 to 35% by weight of fatty acid diester of a polyglycerol; and (C) about 7 to 0.5% by weight of tri- and higher esters of a polyglycerol containing an amount of about 50% and more of $C_{10}$ and/or $C_8$ in the ester component of the polyglycerol; and further wherein the resulting fatty acid polyglycerol ester mixture comprises (A) about 25 to 42% by weight of fatty acid diglycerol ester; (B) about 32 to 43% by weight of fatty acid triglycerol ester; (C) about 43 to 15% by weight of fatty acid tetra- and higher polyglycerol esters; and (D) about 2.5 to 0% by weight free polyglycerol.

In a preferred embodiment, a thickened composition is provided which contains a thickening agent comprising fatty acid esters of a polyglycerol ester mixture within the present invention wherein the esters comprise more than about 90% of $C_{10}$ and/or $C_8$, or more preferably more than about 94% of $C_{10}$ and/or $C_8$ in the ester group of the polyglycerol.

In accordance with another aspect of the present invention, a skincare composition is provided which contains as an additive a fatty acid polyglycerol ester mixture within the present invention comprising, relative to 100 parts by weight of the fatty acid polyglycerol ester mixture, (A) about 35 to 65% by weight of fatty acid monoester of a polyglycerol containing at least about 50% of $C_{10}$ and/or $C_8$ in the ester component of the polyglycerol; (B) about 65 to 35% by weight of fatty acid diester of a polyglycerol; and (C) about 7 to 0 5% by weight of tri- and higher esters of a polyglycerol containing at least about 50% of $C_{10}$ and/or $C_8$ in the ester component of the polyglycerol; and further wherein the resulting fatty acid polyglycerol ester mixture comprises (A) about 25 to 42% by weight of fatty acid diglycerol ester; (B) about 32 to 43% by weight of fatty acid triglycerol ester; (C) about 43 to 15% by weight of fatty acid tetra- and higher polyglycerol esters; and (D) about 2.5 to 0% by weight free polyglycerol.

In a preferred embodiment, a skincare composition is provided which contains an additive comprising fatty acid esters of a polyglycerol ester mixture within the present invention wherein the esters comprise more than about 90% of $C_{10}$ and/or $C_8$, or more preferably more than about 94% of $C_{10}$ and/or $C_8$ in the ester group of the polyglycerol.

In accordance with yet another aspect of the present invention, a cleansing agent is provided which contains a surfactant comprising a fatty acid polyglycerol ester mixture containing a $C_8$ to $C_{24}$ fatty acid ester component and at least one ionogenic and/or amphoteric surfactant, the fatty acid polyglycerol ester mixture comprising, relative to 100 parts by weight of the fatty acid polyglycerol ester mixture, (A) about 20 to 80% by weight of fatty acid monoester of a polyglycerol containing more than about 40% of $C_{10}$ and/or $C_8$ in the ester component of the polyglycerol; (B) about 80 to 20% by weight of fatty acid diester of a polyglycerol; and (C) about 15 to 0% by weight of tri- and higher esters of a polyglycerol containing more than about 40% of $C_{10}$ and/or $C_8$ in the ester component of the polyglycerol; and further wherein the resulting fatty acid polyglycerol ester mixture comprises (A) about 20 to 45% by weight of fatty acid diglycerol ester; (B) about 30 to 45% by weight of fatty acid triglycerol ester; (C) about 50 to 10% by weight of fatty acid tetra- and higher polyglycerol esters; and (D) about 5 to 00% by weight free polyglycerol.

In accordance with still another aspect of the present invention, a cleansing agent is provided which contains as a surfactant a fatty acid polyglycerol ester mixture comprising, relative to 100 parts by weight of the fatty acid polyglycerol ester mixture, (A) about 35 to 65% by weight of fatty acid monoester of a polyglycerol containing at least about 50% of $C_{10}$ and/or $C_8$ in the ester component of the polyglycerol; (B) about 65 to 35% by weight of fatty acid diester of a polyglycerol; and (C) about 7 to 0.5% by weight of tri- and higher esters of the polyglycerol containing at least about 50% of $C_{10}$ and/or $C_8$ in the ester component of the polyglycerol; and further wherein the resulting fatty acid polyglycerol ester mixture comprises (A) about 25 to 42% by weight of fatty acid diglycerol ester; (B) about 32 to 43% by weight of fatty acid triglycerol ester; (C) about 43 to 15% by weight of fatty acid tetra- and higher polyglycerol esters; and (D) about 2.5 to 0% by weight free polyglycerol.

In a preferred embodiment, the cleansing agent comprises a surfactant comprising fatty acid esters of a polyglycerol ester mixture within the present invention containing more than about 90% of $C_{10}$ and/or $C_8$, and more preferably, more than about 94% by weight of $C_{10}$ and/or $C_8$, in the ester group of the polyglycerol.

In yet another preferred embodiment, the cleansing agent additionally comprises electrolytes, preferably inorganic chlorides, in amounts of 0.1 to 8% by weight, preferably 0.7 to 3% by weight, relative to the total weight of the cleansing agent.

In accordance with yet a further aspect of the present invention, a process is provided for preparing fatty acid polyglycerol esters from $C_8$ to $C_{24}$ fatty acid and polyglycerol under acid catalysis, comprising the steps of: (A) reacting a polyglycerol comprising, relative to 100 parts by weight of polyglycerols, (i) about 20 to 45% by weight of diglycerol, (ii) about 30 to 45% by weight of triglycerol, (iii) and about 50 to 10% by weight of tetra- and higher polyglycerols in vacuo with a fatty acid or a fatty acid mixture at about 140° to 200° C., more preferably about 150° to 160° C., in the presence of an acidic catalyst, preferably a compound containing sulfonic acid groups, in a ratio of the polyglycerol mixture to the fatty acid or the fatty acid mixture of about 0.5:1.5 to 1.5:0.5, more preferably about 0.6:1 to 1.2:1, in the presence of an inert gas, preferably nitrogen; (B) continuously removing the resulting reaction product by distillation until an acid number of <3 is attained in the reaction mixture; (C) cooling the reaction mixture to about 60 to 115° C., more preferably about 80° to 110° C.; (D) removing the precipitated polyglycerol fractions; (E) adding an organic solvent to the reaction mixture containing unreacted polyglycerol fractions at about 0° to 100° C., preferably about 20° to 80° C.; (F) adding water to the reaction mixture which contains a neutralizing agent, preferably in approximately equimolar amounts by weight relative to the amount of catalyst and corresponding to the amount of catalyst added; (G) extracting unreacted fractions of polyglycerol with subsequently added water; and (H) separating the organic phase from the organic solvent and residual water by distillation.

In a preferred embodiment, the reaction mixture is allowed to stand for more than about 0.5 h, preferably about 1 to 10 h, after cooling to about 60° to 115° C., preferably about 80° to 110° C., before extraction and/or processing and, if appropriate, precipitated fractions of polyglycerols are separated.

In yet another preferred embodiment, the process further comprises (A) mixing the reaction mixture with an organic chemical solvent or solvent mixture which (i) has a water absorption capacity of less than about 30% by weight, preferably less than about 20% by weight, relative to 100 parts by weight of the organic chemical solvent or solvent mixture, and/or (ii) forms an azeotropic mixture with water during the distillation or in the gas phase; (B) removing the residual (unreacted) polyglycerol fractions; and (C) extracting the residual polyglycerol with water until an amount of less than about 5% by weight, preferably less than about 2.5% by weight, of polyglycerol is contained in the fatty acid polyglycerol ester mixture.

DETAILED DESCRIPTION OF THE PREFERRED EMBODIMENTS

This invention relates to a fatty acid polyglycerol ester mixture characterized by a very specific composition, the distribution of the fatty acid esters and the chain lengths in the ester group. In addition, the invention relates to (a) a thickened composition containing as a thickening agent a fatty acid polyglycerol ester mixture within the present invention; (b) a skincare composition containing as an additive a fatty acid polyglycerol ester mixture within the present invention; and a(c) a cleansing agent containing as a surfactant a fatty acid polyglycerol ester mixture within the present invention. The performance results of a fatty acid polyglycerol ester mixture within the invention are surprisingly superior because, for the first time, a fatty acid polyglycerol ester mixture was discovered which could be produced by a simple process and remain in a liquid state at ambient temperature and, at the same time, be suitable for use as a skincare additive, for example, in view of the stringent dermatological and toxicological standards required for such a use.

A fatty acid polyglycerol ester mixture according to the present invention is a surfactant, and as such, also has surface-active properties in addition to other functions. The total surfactant content of a cleansing agent containing a surfactant comprising a fatty acid polyglycerol ester mixture within the present invention is about 2.5 to 60% by weight, preferably about 7 to 50% by weight, and the residual content of the agent comprises solvents and/or diluents, preferably water, lower alcohols containing $C_1$ to $C_8$ preferably $C_2$ to $C_4$, and/or glycerol in amounts less than about 5% by weight of polyglycerol, or glycerol derivatives and at least one electrolyte and, if appropriate, additives, preferably preservatives, perfumes, colorants, pharmaceutical active substances, standardizing agents for pH regulation, complexing agents for masking metal ions, skincare agents and/or thickeners.

In a preferred embodiment, the total surfactant content of a cleansing agent within the present is about 2.5 to 60% by weight, preferably about 7 to 50% by weight, in which about 0.2 to 60% by weight, more preferably about 1.5 to 45% by weight, of the fatty acid polyglycerol ester mixture according to the invention. A cleansing agent containing a surfactant comprising a fatty acid polyglycerol ester mixture within the present invention also contains about 7 to 0.1% by weight, preferably about 3 to 0.3% by weight, of at least one electrolyte, preferably composed of or containing sodium chloride, and about 90.5 to 39.9% by weight, more preferably about 90 to 49.7% by weight, of a solvent and/or diluent, preferably water, lower alcohols containing $C_1$ to $C_8$, preferably $C_2$ to $C_4$, but not more than about 5% by weight polyglycerol. It additionally contains additives in amounts by weight of about 0.005 to 12 parts by weight (relative to 100 parts by weight of the cleansing agent composed of the surfactant mixture (total surfactant mixture), electrolytes and solvent and/or diluent, preferably about 0.1 to 5 parts by weight, preferably composed of preservatives, perfumes, colorants, pharmaceutical active substances, standardizing agents for pH regulation, complexing agents for masking metal ions, skincare agents and/or thickeners.

The cleansing agent which contains a surfactant comprising a fatty acid polyglycerol ester mixture within the present invention is suitable for use as a detergent, cleaning agent or an agent for cleansing the body, including the hair, for example, a shower gel or shower composition, foam bath composition, liquid hand-cleaning agent or hair shampoo. In addition to exhibiting a milder cleaning action than known cleansing agents, a cleansing agent containing a surfactant comprising a fatty acid polyglycerol ester mixture within the present invention also possesses certain additional properties, such as, for example, a refatting effect and the capacity to impart a pleasant feel to the skin during and after the cleansing process, and an improved flow in the surfactant mixture for the skincare additive. A further advantage of a cleansing agent containing as a surfactant a fatty acid polyglycerol ester mixture within the present inVention is that it is dermatologically and toxicologically harmless.

In a preferred embodiment, a cleansing agent containing as a surfactant a fatty acid polyglycerol ester mixture within the present invention comprises at least one ionogenic surfactant, composed of at least one alkylaryl or alkyl ether sulfate, alkylhydroxyether sulfonate, alkyl sulfate, alkylarylsulfonate, preferably alkylbenzenesulfonate, acylaminopolyglycol ether sulfate, oleinsulfonate, paraffinsulfonate, sulfosuccinic acid ester and/or fatty alcohol ether carboxylate and/or, as amphoteric surfactant, alkylamidobetaine and/or an amphoteric glycerol derivative.

In another preferred embodiment, a cleansing agent containing as a surfactant a fatty acid polyglycerol ester mixture within the present invention comprises an alkyl ether sulfate, alkyl ether sulfonate, alkylhydroxyether sulfonate, aralkyl ether sulfonate and/or alkyl sulfate. As the cation, the surfactant contains Na+, K+, Mg++, NH4+, alkylammonium, alkanolammonium, preferably monoethanolammonium, triethanolammonium, ammonium Na+, and/or NH4+.

In yet another preferred embodiment, a cleansing agent is provided containing as a surfactant a fatty acid polyglycerol ester mixture within the present invention, wherein the cleansing agent has a total surfactant content of about 2.5 to 60% by weight, preferably about 7 to 35% by weight, (relative to 100% by weight of the agent), the surfactant being composed of about 2 to 30% by weight, preferably about 10 to 20% by weight, of the fatty acid polyglycerol ester mixture according to the invention relative to the total surfactant content (100% by weight) and about 98 to 70% by weight, preferably about 90 to 80% by weight, of at least one ionogenic surfactant, composed of at least one alkylaryl or alkyl ether sulfate, alkyl sulfate, alkyl ether sulfonate, alkylhydroxyether sulfonate, polyhydroxyalkyl ether sulfonate, alkylaryl- sulfonate, preferably alkyl benzene sulfonate, acylaminopolyglycol ether sulfate, oleinsulfonate, paraffin- sulfonate, sulfosuccinic acid ester and-/or fatty alcohol ether carboxylate and/or, as amphoteric surfactant, alkylamidobetaine and/or an amphoteric glycerol derivative, but preferably an ionogenic surfactant or surfactant mixture containing or being composed of alkyl ether sulfate, alkylhydroxyether sulfonate, alkylsulfonate and/or alkyl sulfate, which contains as the cation Na+, K+, Mg++, NH4+, monoethanolammonium and/or triethanolammonium, and the residual part is composed of solvents and/or diluents, preferably water, lower alcohols containing $C_1$ to $C_8$, preferably $C_2$ to $C_4$, and/or glycerol or glycerol derivatives, electrolytes and, if appropriate, additives, preferably preservatives, perfumes, colorants, pharmaceutical active substances, standardizing agents for pH regulation, complexing agents for masking metal ions, skincare agents and/or thickeners, or contains these.

In a further preferred embodiment, a cleansing agent within the present invention contains about 7 to 0.1% by weight, preferably about 3 to 0.3% by weight, of at least one electrolyte, preferably composed of or containing sodium chloride and/or ammonium chloride, about 90.5 to 39.9% by weight, preferably about 90 to 64.7% by weight, of a solvent and/or diluent, preferably water, lower alcohols containing $C_1$ to $C_8$, preferably $C_2$ to $C_4$, and/or diols containing $C_3$ to $C_8$, preferably $C_3$ to $C_6$, and additives in amounts by weight of 0.005 to 12 parts by weight (relative to 100 parts by weight of the cleansing agent comprising the surfactant mixture, electrolyte and solvent and/or diluent), preferably about 0.1 to 5 parts by weight, preferably composed of preservatives, perfumes, colorants, pharmaceutical active substances, standardizing agents for pH regulation, complexing agents for masking metal ions, skincare agents and/or thickeners.

Alkyl ether sulfates, alkylarylsulfonates, alkyl sulfates and alkylsulfonates, esters and olefinsulfonates thereof suitable for use in the present invention are those with a C number of 8 to 22, preferably 10 to 18. In the case of surfactants provided with a hydrophobic radical in the form of a saturated, unsaturated or branched hydrocarbon radical, the hydrophobic radical can also be connected to the sulfate and/or sulfonate group via a phenyl radical and/or via other heteroatoms, for example oxygen, for example as alkyl ether sulfates. Preferably alkali metal lauryl ether sulfate, in particular sodium lauryl ether sulfate, acylaminopolyglycol ether sulfates, preferably in the form of the alkanolamine compound, in particular triethanolamine salt, sulfosuccinic acid ester or sulfodicarboxylic acid ester, alkali metal benzenesulfonate and ammonium alkylbenzenesulfonate, preferably sodium alkyl benzenesulfonate or ammonium alkyl benzenesulfonate or triethanolammonium alkyl benzenesulfonate and the like are employed.

Alkyl ether sulfates suitable for use in the present invention are compounds of the general formula $RO(C_2H_4O)_nSO_3M$, in which R represents an alkyl chain having 10 to 18, preferably 12 to 14, carbon atoms, n represents numbers from 1 to 10 and M represents a cation. These alkyl ether sulfates are obtained by ethoxylation of monohydric alcohols having 10 to 18 carbon atoms to the desired degree of ethoxylation and subsequent sulfation and/or neutralization. The acidic sulfation products or the sulfonates can be neutralized by alkalis, ammonia, amines or alkanolamines and/or by magnesium hydroxide. Alkylhydroxyether sulfonates or polyhydroxyalkyl ether sulfates suitable for use in the present invention are preferably those containing $C_{10}$ to $C_{18}$, preferably $C_{12}$ to $C_{14}$, in the fatty acid chain.

Electrolytes which are conventionally employed in cleansing agents designed for dermatological use are suitable for use as electrolytes in addition to sodium chloride and/or ammonium chloride.

A cleansing agent within the present invention can also contain other compounds. Exemplary of such compounds are colloids, for example, derivatives of cellulose or starch, disinfectants, fungicidal or antibacterial agents, and anticorrosive agents.

Another aspect of the present invention relates to a process for the preparation of fatty acid polyglycerol esters from $C_8$ to $C_{24}$ fatty acid and polyglycerol under acid catalysis. According to the present invention, a mixture is employed as the polyglycerol which comprises (relative to 100 parts by weight of polyglycerols employed) (A) about 20 to 45% by weight of diglycerol, (B) about 30 to 45% by weight of triglycerol; and (C) about 50 to 10% by weight of tetra- and higher polyglycerols. This mixture is reacted in vacuo with the fatty acid or the fatty acid mixture at about 140° to 200° C., preferably about 150° to 160° C., in the presence of an acidic catalyst, preferably a compound containing sulfonic acid groups, in a ratio of the polyglycerol mixture to the fatty acid or the fatty acid mixture of about 0.5:1.5 to 1.5:0.5, preferably about 0.6:1 to 1.2:1, in the presence of an inert gas, preferably nitrogen, and the resulting reaction product is continuously removed by distillation until an acid number of <3 is attained in the reaction mixture. The reaction mixture is cooled to about 60° to 115° C., preferably about 80° to 110° C., and any precipitated polyglycerol fractions are removed, after which an organic solvent is added to the reaction mixture containing unreacted polyglycerol fractions at about 0° to 100° C., preferably about 20° to 80° C., and unreacted fractions of polyglycerol are extracted with subsequently added water, which contains a neutralizing agent, preferably in approximately equimolar amounts by weight relative to the amount of catalyst, corresponding to the amount of catalyst added, in at least one extraction step. The separated organic phase is separated by distillation from the organic solvent employed and the residual water content in order to finally prepare the fatty acid polyglycerol ester mixture.

In a preferred embodiment, the reaction mixture is allowed to stand for more than about 0.5 h, preferably about 1 to 10 h, after cooling to about 60° to 115° C., preferably about 80° to 110° C., before extraction and/or processing and, if appropriate, precipitated fractions of polyglycerols are separated.

In another preferred embodiment, the reaction mixture is mixed to extract or remove the residual (unreacted) polyglycerol fractions with an organic chemical solvent or solvent mixture which has a water absorption capacity of less than about 30% by weight, preferably less than about 20% by weight (relative to 100 parts by weight of the organic chemical solvent or solvent mixture) and/or forms an azeotropic mixture with water during the distillation or in the gas phase. The residual polyglycerol is then extracted with water. The free polyglycerol is preferably extracted or separated until an amount of less than about 5% by weight, preferably less than about 2.5% by weight, of polyglycerol is contained in the fatty acid polyglycerol ester mixture prepared according to the invention.

The invention also relates to the use of a fatty acid polyglycerol ester mixture within the present invention and a fatty acid polyglycerol ester mixture prepared according to a process within the present invention as a solubilization agent or as an emulsifier, preferably for solubilizing ethereal oils and perfume oils in water.

A fatty acid polyglycerol ester mixture within the invention can be used in a versatile manner, for example as a thickening agent, skincare additive, a surfactant for a cleansing agent, such as a detergent, cleaning agent, body cleaning agent, bath additive, as an additive for foodstuffs, in particular fats, fat replacements, confectionery and chocolate goods; as an additive for medicaments, ointments, pharmaceutical preparations; additive for disinfectants, for cosmetic preparations, for colors, in particular body colors and colors for children and the like. The versatile applicability results, inter alia, on the one hand because the fatty acid polyglycerol ester mixture within the present invention is easily processed, for example processing at room temperature where the processing of numerous other products is facilitated with the aid of an agent within the invention, and on the other hand, because the fatty acid polyglycerol ester mixture is toxicologically and ecologically harmless, neutral or beneficial to the skin and body and even edible. Cosmetic preparations containing a fatty acid polyglycerol ester mixture within the invention as an additive exhibit optimal results, leaving the skin feeling soft and smooth. When used on the skin, for example as an additive in cosmetic preparations, skin disinfectants, ointments, liniments and the like, a fatty acid polyglycerol ester mixture within the invention has a refatting action.

Without further elaboration, it is believed that one skilled in the art can, using the preceding description, utilize the present invention to its fullest extent. The following preferred specific embodiments are therefore, to be construed as merely illustrative, and not limitative of the remainder of the disclosure in any way whatsoever.

EXAMPLE 1

Polyglycerol caprate

A mixture of 704 g of polyglycerol (composed of about 30% diglycerol, about 48% triglycerol, about 13% tetraglycerol and about 9% higher oligomers), 688 g of capric acid, 2.8 g of dodecylbenzenesulfonic acid and 1.1 g of hypophosphorous acid in a 2-liter four-necked flask equipped with a stirrer, water separator, thermometer and gas inlet tube was heated to a maximum of 165° C. at 400 to 40 mbar for about 4 hours with stirring and simultaneous passage of inert gas, while the water produced by the reaction was continuously removed by distillation. When an acid number of <2 was attained, the reaction mixture was cooled to about 60 to 65° C. and unreacted fractions of polyglycerol were removed as described below.

The reaction mixture was dissolved in ethyl acetate (the same amount by volume) and extracted with water in three steps. In the first step, an amount of a sodium hydroxide solution corresponding to the acid number was added to the water. The total amount of water used for extraction was about 87% by volume of the ester employed. The total amount of polyglycerol extracted after removal of the solvents by distillation was 124 g. The organic phase remaining after the extraction was evaporated in vacuo.

| Characteristic numbers | |
|---|---|
| Acid number: | 0.6 |
| Hydrolysis number: | 184.9 |
| Viscosity at 25° C.: | 2100 mPa.s |
| Color according to Gardner: | 2-3 |
| Amounts of the ester in % by weight | |
| Monoester: | about 40 |
| Diester: | about 50 |
| Higher esters: | about 10 |

EXAMPLE 2

Polyglycerol caprate

A mixture of 704 g of polyglycerol (composed of about 30% diglycerol, about 48% triglycerol, about 13% tetraglycerol and about 9% higher oligomers), 616 g of capric acid, 2.8 g of dodecylbenzenesulfonic acid and 1.1 g of hypophosphorous acid in a 2-liter four-necked flask equipped with a stirrer, water separator, thermometer and gas inlet tube was heated to a maximum of 165° C. at 400 to 40 mbar for about 4 hours with stirring and simultaneous passage of inert gas, while the water produced by the reaction was continuously removed by distillation. When an acid number of <2 was attaine,d the reaction mixture was cooled to about 60 to 65° C. and unreacted fractions of polyglycerol were removed as described below.

The reaction mixture was dissolved in ethyl acetate (the same amount by volume) and extracted with water in three steps. In the first step, an amount of a sodium hydroxide solution corresponding to the acid number was added to the water. The total amount of the water used for extraction was about 87% by volume of the ester employed. The total amount of polyglycerol extracted after removal of the solvents by distillation was 44 g. The organic phase remaining after the extraction was evaporated in vacuo.

| Characteristic numbers | |
| --- | --- |
| Acid number: | 0.6 |
| Hydrolysis number: | 198.9 |
| Viscosity at 25° C.: | 2000 mPa.s |
| Color according to Gardner: | 1-2 |
| Amounts of the ester in % by weight | |
| Monoester: | about 35 |
| Diester: | about 55 |
| Higher esters: | about 10 |

EXAMPLE 3

Polyglycerol cocoa

A mixture of 717 g of polyglycerol (composed of about 30% diglycerol, about 39% triglycerol, about 19% tetraglycerol and about 12% higher oligomers), 856 g of coconut fatty acid, 2.8 g of dodecylbenzenesulfonic acid and 1.1 g of hypophosphorous acid in a 2-liter four-necked flask equipped with a stirrer, water separator, thermometer and gas inlet tube was heated to a maximum of 165° C. at 400 to 40 mbar for about 4 hours with stirring and simultaneous passage of inert gas, while the water produced by the reaction was continuously removed by distillation. When an acid number of <2 was attained, the reaction mixture was cooled to about 60 to 65° C. and unreacted fractions of polyglycerol were removed as described below.

The reaction mixture was dissolved in ethyl acetate (the same amount by volume) and extracted with water in three steps. In the first step, an amount of a sodium hydroxide solution corresponding to the acid number was added to the water. The total amount of the water used for extraction was about 87% by volume of the ester employed. The total amount of polyglycerol extracted after removal of the solvent by distillation was 93 g. The organic phase remaining after the extraction was evaporated in vacuo.

| Characteristic numbers | |
| --- | --- |
| Acid number: | 1.5 |
| Hydrolysis number: | 161.5 |
| Viscosity at 25° C.: | 5800 mPa.s |
| Color according to Gardner: | 3 |
| Amounts of the ester in % by weight | |
| Monoester: | about 40 |
| Diester: | about 50 |
| Higher esters: | about 10 |

EXAMPLE 4

Polyglycerol caprate

Six hundred and eighty-eight (688) grams of capric acid were continuously added in a metered fashion during the course of 3 hours to 896 g of polyglycerol (composed of about 30% diglycerol, about 48% triglycerol, about 13% tetraflycerol and about 9% higher oligomers), 2.8 g of dodecylbenzenesulfonic acid and 1.1 g of hypophosphorous acid contained in a 2-liter four-necked flask equipped with a stirrer, water separator, thermometer and gas inlet tube and maintained at a temperature of a maximum of 165°0 C. and 100 to 40 mbar with stirring and simultaneous passage of inert gas, while the water produced by the reaction was removed by distillation during the entire reaction period. When an acid number of <2 was attained, the reaction mixture was cooled to about 60° to 65° C. and unreacted fractions of polyglycerol were removed as described below.

The reaction mixture was dissolved in ethyl acetate (the same amount by volume) and extracted with water in three steps. In the first step, an amount of a sodium hydroxide solution corresponding to the acid number was added to the water. The total amount of the water used for extraction was about 87% by volume of the ester employed. The total amount of polyglycerol extracted after removal of the solvent by distillation was 203 g. The organic phase remaining after the extraction was evaporated in vacuo.

| Characteristic numbers | |
| --- | --- |
| Acid number: | 0.8 |
| Hydrolysis number: | 168.5 |
| Viscosity at 25° C.: | 6012 mPa.s |
| Color according to Gardner: | 2-3 |
| Amounts of the ester in % by weight | |
| Monoester: | about 70 |
| Diester: | about 25 |
| Higher esters: | about 5 |

EXAMPLE 5

Polyglycerol caorate

A mixture of 896 g of polyglycerol (composed of about 30% diglycerol, about 48% triglycerol, about 13% tetraglycerol and about 9% higher oligomers), 688 g of capric acid, 2.8 g of dodecylbenzenesulfonic acid and 1.1 g of hypophosphorous acid contained in a 2-liter four-necked flask equipped with a stirrer, water separator, thermometer and gas inlet tube was heated to a maximum of 165° C. at 400 to 40 mbar for about 4 hours with stirring and simultaneous passage of inert gas, while the water produced by the reaction was continuously removed by distillation. When an acid number of <2 was attained, the reaction mixture was cooled to about 60° to 65° C. and unreacted fractions of polyglycerol were removed as described below.

The reaction mixture was dissolved in ethyl acetate (the same amount by volume) and extracted with water in three steps. In the first step, an amount of a sodium hydroxide solution corresponding to the acid number was added to the water. The total amount of the water used for extraction was about 87% by volume of the ester employed. The total amount of polyglycerol extracted after removal of the solvents by distillation was 228 g. The organic phase remaining after the extraction was evaporated in vacuo.

| Characteristic numbers | |
|---|---|
| Acid number: | 1.0 |
| Hydrolysis number: | 173.3 |
| Viscosity at 25° C.: | 4329 mPa.s |
| Color according to Gardner: | 2-3 |
| Amounts of the ester in % in weight | |
| Monoester: | about 60 |
| Diester: | about 32 |
| Higher esters: | about 8 |

EXAMPLE 6

Comparison of the Thickening Properties of the Ester Before or After the Extraction of Unreacted Fractions of Polyglycerol Polyglycerol caprate was synthesized according to the methodology of Example 1. The polyglycerol caprate was added in increasing amounts to a 14% strength sodium lauryl ether sulfate solution which contained 2% of sodium chloride and the resulting viscosity was measured:

| 97 g of sodium lauryl ether sulfate solution + 3 g of polyglycerol caprate; viscosities resulting therefrom: | |
|---|---|
| 4000 mPa.s without extraction | 7200 mPa.s after extraction. |

EXAMPLE 7

Foam and Thickening Powers

A polyglycerol caprate synthesized according to the methodology of Example 1 was added in increasing amounts to a 14% strength sodium lauryl ether sulfate solution which contained 2% of sodium chloride and the resulting viscosity was measured:

| | |
|---|---|
| 1. Solution* without addition | 14 mPa.s |
| 2. 99 g of solution + 1 g of polyglycerol caprate | 187 mPa.s |
| 3. 98 g of solution + 2 g of polyglycerol caprate | 935 mPa.s |
| 4. 97 g of solution + 3 g of polyglycerol caprate | 6600 mPa.s |

* = sodium lauryl ether sulfate solution containing 2% sodium chloride

EXAMPLE 8

Determination of foam according to Ross/Miles DIN 53 902 Part 2

| | Development of foam after: | | |
|---|---|---|---|
| | 30 seconds | 3 minutes | 5 minutes |
| From solution 1** without addition | 156 mm | 159 mm | 158 mm |
| From solution 4*** + 3 g of polyglycerol caprate | 171 mm | 162 mm | 156 mm |

*In a 1 g/l active substance solution in distilled water at 40° C.
** = 98 g of sodium lauryl ether sulfate solution containing 2% of sodium chloride + 2 g of polyglycerol caprate
*** = 97 g of sodium lauryl ether sulfate solution containing 2% of sodium chloride + 3 g of polyglycerol caprate The results show that in addition to a considerable thickening action a distinct improvement in the foaming power also occurs. After 30 seconds, there is an increase from 156 mm to 171 mm or about 10%.

EXAMPLE 9

| Formulations | |
|---|---|
| 1. Hair shampoo, mild, 12% active content | |
| Sodium lauryl ether sulfate, 28% strength | 21.4% by wt % |
| Coconutamidopropylbetaine, 30% strength | 6.7% by wt % |
| Disodium fatty alcohol polyglycol ether sulfosuccinate, 40% strength | 5.0% by wt % |
| Polyglycerol caprate prepared according to the methodology of Examples 4 or 5 | 2.0% by wt % |
| Sodium chloride | 1.5% by wt % |
| Perfume, preservative, standardizing agent and water | to 100% by wt % |
| Viscosity, measured using a rotary viscometer: | |
| VT 181, Haake, at 20° C. | 3150 mPa.s |
| Foam number according to Ross/Miles (1 g/l of active substance at 40° C. in distd. water) | 176/171/170 |
| Cold stability of the formulation | <0° C. |
| 2. Hair shampoo, mild, 16% active content | |
| Sodium lauryl ether sulfate, 28% strength | 20.0% by wt % |
| Coconutamidopropylbetaine, 30% strength | 8.9% by wt % |
| Disodium fatty alcohol polyglycol ether sulfosuccinate, 40% strength | 13.4% by wt % |
| Polyglycerol caprate prepared according to the methodology of Examples 1 or 4 | 2.7% by wt % |
| Sodium chloride | 1.5% by wt % |
| Perfume, preservative, standardizing agent and water | to 100% by wt % |
| Viscosity at 20° C. | 1400 mPa.s |
| Foam number according to Ross/Miles (1 g/l of active substance at 40° C. in distd. water) | 167/164/161 |
| Cold stability of the formulation | <0° C. |
| 3. Foam bath, 20% active substance | |
| Sodium lauryl ether sulfate, 28% strength | 28.6% by wt % |
| Coconutamidopropylbetaine, 30% strength | 6.7% by wt % |
| Disodium fatty alcohol polyglycol ether sulfosuccinate, 40% strength | 17.5% by wt % |
| Polyglycerol caprate prepared according to the methodology of Examples 1, 4 or 5 | 3.0% by wt % |
| Sodium chloride | 1.0% by wt % |
| Perfume, preservative, standardizing agent and water | to 100% by wt % |
| Viscosity at 20° C. | 1300 mPa.s |
| Foam number according to Ross/Miles (1 g/l of active substance at 40° C. in distd. water) | 164/159/158 |
| Cold stability of the formulation | <0° C. |
| 4. Liquid soap, 13.5% active content | |
| Sodium lauryl ether sulfate, 28% strength | 7.1% by wt % |
| Monoethanolamine lauryl sulfate, 30% strength | 12.0% by wt % |
| Sodium polyethylene glycol-6-coconutamidocarboxylate, 30% strength | 15.0% by wt % |
| Disodium fatty alcohol polyglycol ether sulfosuccinate, 40% strength | 5.0% by wt % |
| Polyglycerol caprate prepared according to methodology of Examples 4 or 5 | 1.5% by wt % |
| Sodium chloride | 1.0% by wt % |
| Perfume, preservative, standardizing | to 100% by wt % |

-continued

| Formulations | |
|---|---|
| agent and water | |
| Viscosity at 20° C. | 660 mPa.s |
| Foam number according to Ross/Miles (1 g/l of active substance at 40° C. in distd. water) | 167/154/138 |
| Cold stability of the formulation | <0° C. |
| 5. Skincare oil bath | |
| Rosemary oil | 42% by wt % |
| Polyglycerol caprate prepared according to the methodology of Examples 2 or 4 (as skincare additive and solubilizer) | 43% by wt % |
| Water, completely demineralized | 15% by wt % |

What is claimed is:

1. A fatty acid polyglycerol ester mixture containing a $C_8$ to $C_{24}$ fatty acid ester component, said fatty acid polyglycerol ester mixture comprising, relative to 100 parts by weight of said fatty acid polyglycerol ester mixture,
   (A) about 20 to 80% by weight of fatty acid monoester of a polyglycerol containing more than about 40% selected from the group consisting of $C_{10}$ and $C_8$ in the ester component of said polyglycerol;
   (B) about 80 to 20% by weight of fatty acid diester of a polyglycerol; and
   (C) about 15 to 0% by weight of tri- and higher esters of a polyglycerol containing more than about 40% selected from the group consisting of $C_{10}$ and $C_8$ in the ester component of said polyglycerol; and further wherein said fatty acid polyglycerol ester mixture comprises
   (A) about 20 to 45% by weight of fatty acid diglycerol ester;
   (B) about 30 to 45% by weight of fatty acid triglycerol ester;
   (C) about 50 to 10% by weight of fatty acid tetra- and higher polyglycerol esters; and
   (D) about 5 to 0% by weight free polyglycerol.

2. A fatty acid polyglycerol ester mixture as claimed in claim 1, wherein said fatty acid polyglycerol ester mixture comprises, relative to 100 parts by weight of the fatty acid polyglycerol ester mixture,
   (A) about 35 to 65% by weight of fatty acid monoester of a polyglycerol containing at least about 50% selected from the group consisting of $C_{10}$ and $C_8$ in the ester component of said polyglycerol;
   (B) about 65 to 35% by weight of fatty acid diester of a polyglycerol; and
   (C) about 7 to 0.5% by weight of tri- and higher esters of a polyglycerol containing at least about 50% selected from the group consisting of $C_{10}$ and $C_8$ in the ester component of said polglycerol; and further wherein said fatty acid polyglycerol ester mixture comprises
   (A) about 25 to 42% by weight of fatty acid diglycerol ester;
   (B) about 32 to 43% by weight of fatty acid triglycerol ester;
   (C) about 43 to 15% by weight of fatty acid tetra- and higher polyglycerol esters; and
   (D) about 2.5 to 0% free polyglycerol.

3. A fatty acid polyglycerol ester mixture as claimed in claim 1, wherein said fatty acid esters of said polyglycerol contain more than about 90% selected from the group consisting of $C_{10}$ and $C_8$ in said ester group of said polyglycerol.

4. A fatty acid polyglycerol ester mixture as claimed in claim 2, wherien said fatty acid esters of said polglycerol contain more than about 90% selected from the group consisting of $C_{10}$ and $C_8$ in said ester group of said polyglycerol.

5. A thickening composition containing as a thickening agent an effective amount of a fatty acid polyglycerol ester mixture according to claim 1.

6. A thickened composition containing as a thickening agent an effective amount of a fatty acid polyglycerol ester mixture according to claim 2.

7. A thickened composition as claimed in claim 5, wherein said fatty acid esters of said polyglycerol contain more than about 90% selected from the group consisting of $C_{10}$ and $C_8$ in said ester group of said polyglycerol.

8. A thickened composition as claimed in claim 6, wherein said fatty acid esters of said polyglycerol contain more than about 90% selected from the group consisting of $C_{10}$ and $C_8$ in said ester group of said polyglycerol.

9. A skincare composition containing as an additive an effective a amount of a fatty acid polyglycerol ester mixture according to claim 1.

10. A skincare composition containing as an additive an effective amount of a fatty acid polyglycerol ester mixture according to claim 2.

11. A skincare composition as claimed in claim 9, wherein said fatty acid esters of said polyglycerol contain more than about 90% selected from the group consisting of $C_{10}$ and $C_8$ in said ester group of said polyglycerol.

12. A skincare composition containing as claimed in claim 10, wherein said fatty acid esters of said polglycerol contain more than about 90% selected from the group consisting of $C_{10}$ and $C_8$ in said ester group of said polyglycerol.

13. A cleansing agent comprising as a furfactant an effective amount of a fatty acid polyglycerol ester mixture according to claim 1.

14. A cleansing agent containing as a furfactant an effective amount of a fatty acid polyglycerol ester mixture as claimed in claim 2.

15. A cleansing agent as claimed in claim 13, wherein said fatty acid esters of said polyglycerol contain more than about 90% selected from the group consisting of $C_{10}$ and $C_8$ in said ester group of said polyglycerol.

16. A cleansing agent as claimed in claim 14, wherein said fatty acid esters of said polyglycerol contain more than about 90% selected from the group consisting of $C_{10}$ and $C_8$ in said ester group of said polyglycerol.

17. A process for preparing fatty acid polyglycerol esters from $C_8$ to $C_{24}$ fatty acids and polyglycerol under acid catalysis, comprising the steps of:
   (A) reacting a polyglycerol comprising, relative to 100 parts by weight of polyglycerols, (i) 20 to 45% by weight of diglycerol, (ii) 30 to 45% by weight of triglycerol, and (iii) 50 to 10% by weight of tetr- and higher polyglycerols in vacuo with a fatty acid or a fatty acid mixture at 140 to 200° C in the presence of an acidic catalyst in a ratio of said polyglycerol mixture to said fatty acid or said fatty acid mixture of 0.5: to 1.5:0.5 in the presence of an inert gas;
   (B) continuously removing resulting reaction product by distillation until an acid number of <3 is attained in the reaction mixture;
   C) cooling said reaction mixture to 60° to 115° C.;

(D) removing precipitated polyglycerol fractions;
(E) adding an organic solvent to said reaction mixture containing unreacted polyglycerol fractions at 0° to 100° C.;
(F) adding water to said reaction mixture, said water containing a neutralizing agent;
(G) extracting unreacted fractions of polyglycerol by adding water; and
(H) separating the organic phase from the organic solvent and residual water by distillation.

18. A process as claimed in claim 17, wherein in step (A), said polyglycerol is reacted with said fatty acid or said fatty acid mixture at 150° to 160° C.

19. A process as claimed in claim 17, wherein said acidic catalyst is a compound containing sulfonic acid groups.

20. A process as claimed in claim 17, wherein said ratio of said polyglycerol mixture to said fatty acid or said fatty acid mixture ranges from 0.6:1 to 1.2:1.

21. A process as claimed in claim 17, wherein said inert gas is nitrogen.

22. A process as claimed in claim 17, wherein in step (C), said reaction mixture is cooled to 20 to 80° C.

23. A process as claimed in claim 17, wherein in step (E) said organic solvent is added to said reaction mixture containing unreacted polyglycerol fractions at 80° to 110° C.

24. A process as claimed in claim 17, wherein in step (F) said neutralizing agent in said water is in approximately equimolar amounts by weight relative to the amount of catalyst added.

25. A process as claimed in claim 17, comprising the further steps of:
(A) allowing said reaction mixture to stand for more than 0.5 hour after cooling to 60° to 115° C., before extracting; and
(B) separating precipitated fractions of polyglycerols.

26. A process as claimed in claim 25, wherein in step (A) said reaction mixture is allowed to stand for m 1 to 10 hours.

27. A process as claimed in claim 25, wherein in step (A) said reaction mixture is allowed to stand for more than 0.5 hour after cooling to 80 to 110° C.

28. A process as claimed in claim 17, further comprising the step of:
(A) mixing said reaction mixture with an organic chemical solvent or solvent mixture which (i) has a water absorption capacity of less than 30% by weight, preferably less than 20% by weight, relative to 100 parts by weight of the organic chemical solvent or solvent mixture, and (ii) forms an azeotropic mixture with water during distillation or in the gas phase;
(B) removing residual (unreacted) polyglycerol fractions; and
(C) extracting said residual polyglycerol with water until said fatty acid polyglycerol ester mixture contains less than 5% by weight polyglycerol.

29. A process as claimed in claim 28, wherein said fatty acid polyglycerol ester mixture contains less than 2.5% by weight polyglycerol.

* * * * *